US012653771B2

(12) United States Patent
Lee et al.

(10) Patent No.: US 12,653,771 B2
(45) Date of Patent: Jun. 16, 2026

(54) COMPOSITION FOR REMEDYING INGROWN (TOE)NAIL

(71) Applicant: Misook Lee, Incheon (KR)

(72) Inventors: Misook Lee, Incheon (KR); Dae Beom Lee, Incheon (KR)

(73) Assignee: Misook Lee, Incheon (KR)

( * ) Notice: Subject to any disclaimer, the term of this patent is extended or adjusted under 35 U.S.C. 154(b) by 266 days.

(21) Appl. No.: 18/694,772

(22) PCT Filed: Sep. 22, 2022

(86) PCT No.: PCT/KR2022/014155

§ 371 (c)(1),
(2) Date: Mar. 22, 2024

(87) PCT Pub. No.: WO2023/048474

PCT Pub. Date: Mar. 30, 2023

(65) Prior Publication Data

US 2025/0114293 A1 Apr. 10, 2025

(30) Foreign Application Priority Data

Sep. 23, 2021 (KR) ........................ 10-2021-0125885

(51) Int. Cl.

| | |
|---|---|
| ***A61K 8/893*** | (2006.01) |
| ***A61K 8/35*** | (2006.01) |
| ***A61K 8/81*** | (2006.01) |
| ***A61Q 3/02*** | (2006.01) |

(52) U.S. Cl.

CPC ................ *A61K 8/893* (2013.01); *A61K 8/35* (2013.01); *A61K 8/8152* (2013.01); *A61Q 3/02* (2013.01); *A61K 2800/81* (2013.01); *A61K 2800/95* (2013.01)

(58) Field of Classification Search

None

See application file for complete search history.

(56) References Cited

U.S. PATENT DOCUMENTS

| | | | |
|---|---|---|---|
| 2012/0191033 | A1 | 7/2012 | Hillebrand |
| 2016/0250136 | A1 | 9/2016 | Bryson et al. |
| 2018/0092827 | A1 | 4/2018 | Sheran et al. |

FOREIGN PATENT DOCUMENTS

| | | | |
|---|---|---|---|
| KR | 10-1565692 | B1 | 11/2015 |
| KR | 10-1646004 | B1 | 8/2016 |
| KR | 10-2017-0069442 | A | 6/2017 |
| KR | 10-2019-0098956 | A | 8/2019 |
| KR | 10-2021734 | B1 | 9/2019 |
| KR | 10-2021-0077394 | A | 6/2021 |

OTHER PUBLICATIONS

International Search Report for PCT/KR2022/014155 dated Dec. 27, 2022.

Written Opinion for PCT/KR2022/014155 dated Dec. 27, 2022.

*Primary Examiner* — Nannette Holloman

(74) *Attorney, Agent, or Firm* — Sughrue Mion, PLLC

(57) ABSTRACT

A composition for remedying an ingrown fingernail or toenail contains a siloxane resin, an acrylate compound, and a photoinitiator. The composition, when applied to ingrown fingernail or toenail, forms an inverse curl in the direction opposite to the curved direction of the ingrown fingernail or toenail, and thus the effect of remedying an ingrown fingernail or toenail can be provided. In addition, the composition is capable of preventing a cured material from being separated from the surface of a fingernail or toenail while maximizing the degree of curl thereof through optimal mixing of the composition, preventing residues from being appearing after curing, and controlling the heat caused by reaction heat so that the temperature thereof does not rise, and thus has the effect of remedying an ingrown fingernail or toenail and excellent use convenience.

20 Claims, 2 Drawing Sheets

【FIG. 1】
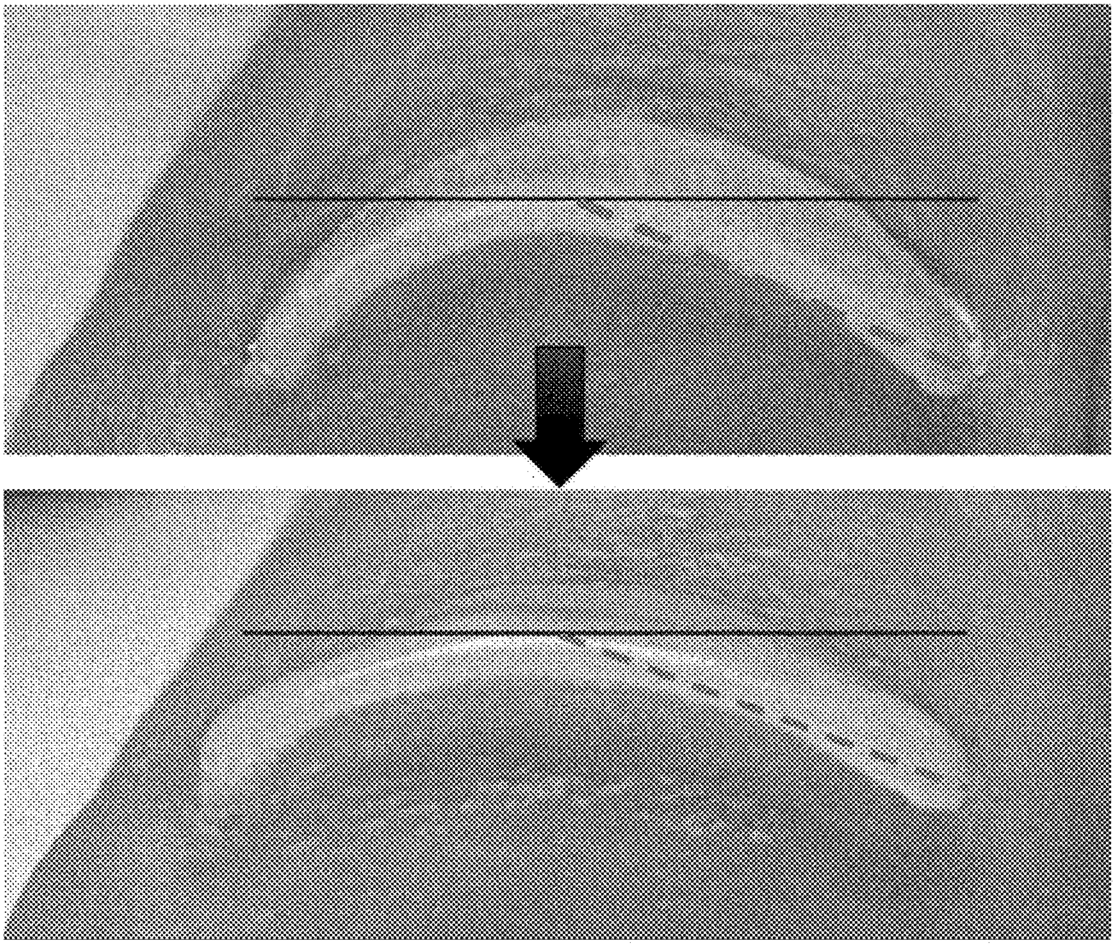

【FIG. 2】
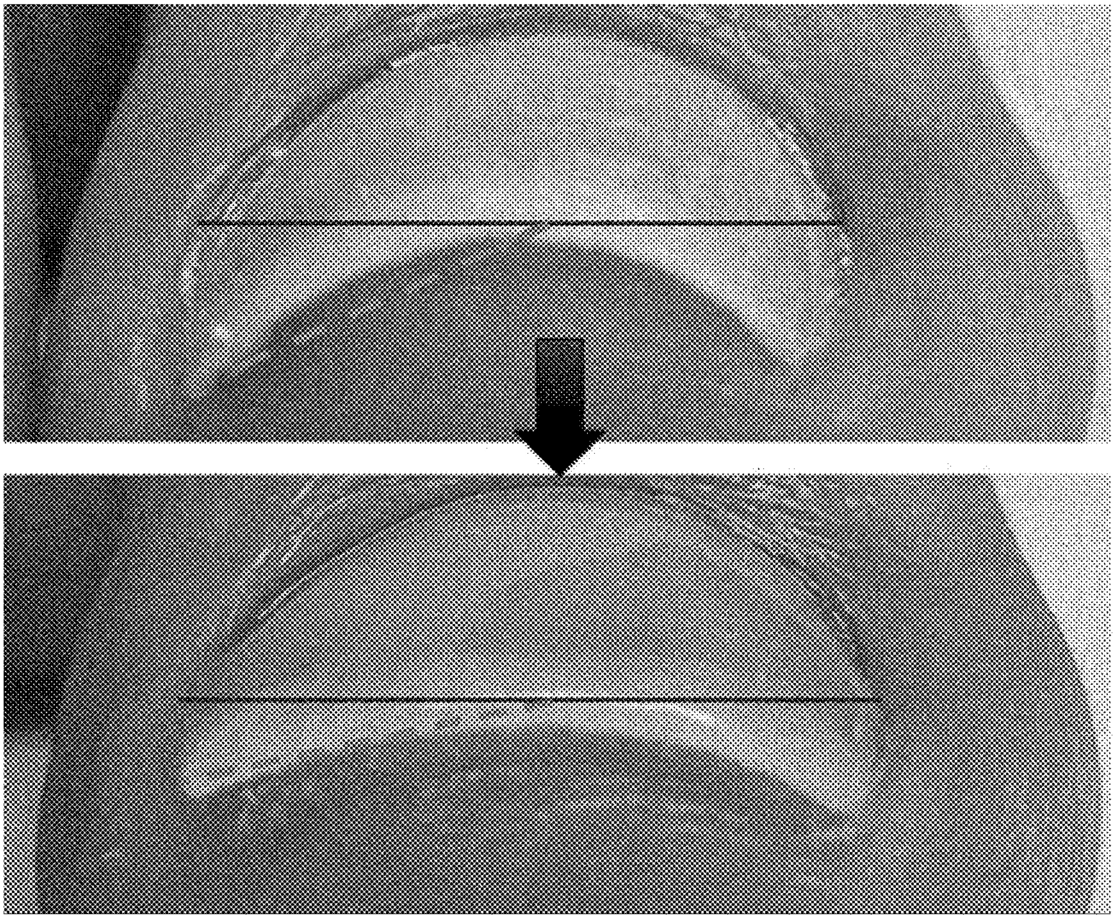

COMPOSITION FOR REMEDYING INGROWN (TOE)NAIL

CROSS REFERENCE TO RELATED APPLICATIONS

This application is a National Stage of International Application No. PCT/KR2022/014155 filed Sep. 22, 2022, claiming priority based on Korean Patent Application No. 10-2021-0125885 filed Sep. 23, 2021.

TECHNICAL FIELD

The present disclosure relates to a composition for remedying an ingrown fingernail or toenail, and more particularly, to a composition capable of remedying an ingrown fingernail or toenail by inducing an inverse curl in the direction opposite to the curved direction of the ingrown fingernail or toenail when applied to the ingrown fingernail or toenail and then cured.

BACKGROUND ART

An ingrown (toe)nail is a disease in which a fingernail or toenail digs into the flesh, causing inflammation and pain. The ingrown fingernail or toenail may be caused by a variety of reasons, such as when the natural curvature of the fingernail or toenail becomes worse due to obesity or aging, when the shape of the fingernail or toenail is deformed due to neglect of athlete's foot for a long time, or when the toenail continuously presses on the flesh outside the toenail when wearing tight shoes for a long time.

Such an ingrown fingernail or toenail disease often occurs in toenails, especially a big toenail, and since ingrown toenails are considerably thicker than normal toenails, the toenails dig into the flesh with greater force, causing more inflammation and pain. If the inflammation worsens, it can cause serious inconveniences in daily life, such as odor, worsening pain, difficulty walking, and worsening of symptoms by wearing shoes.

As a corrective device for treating such an ingrown fingernail or toenail disease, Korean Patent Publication No. 10-1565692 discloses a corrective device that correctly remedies an ingrown toenail into a normal toenail by attaching an elastic leaf spring to the toenail. However, when such a corrective device is attached to the toenail, the user may feel uncomfortable during daily life or walking due to the fit, and continuous remedy may be difficult when going out because it is difficult to wear shoes with the corrective device inserted due to a size of the device.

In order to solve the inconveniences of such a corrective device, a technique for remedying ingrown toenails by applying a coating agent to the toenails has been proposed. As an example, Korea Patent Publication No. 10-2021734 discloses a technology that shows the effect of remedying the ingrown toenails by coating the toenails with a coating agent containing nitrocellulose, acrylic resin, dibutyl phthalate, butyl acetate, valproic acid, and caffeic acid ester.

However, there was a disadvantage that the surface of the toenail had to be polished in order to remedy the ingrown toenails using the coating agent. In addition, the above technology is intended to provide flexibility to the toenail while softening the surface of the toenail using the coating agent, and has a limitation in that it only plays a secondary role in the remedy, has no direct relationship with the effect of remedying, and takes a long time for the effect to appear.

Accordingly, there is a need to develop a technology for remedying an ingrown fingernail or toenail that may provide excellent effect of remedying without using a corrective device that causes discomfort to the user.

DISCLOSURE

Technical Problem

The purpose of the present disclosure is to provide a composition capable of remedying an ingrown fingernail or toenail by inducing an inverse curl in a direction opposite to the curved direction of the ingrown fingernail or toenail.

Technical Solution

To achieve the above object, the present disclosure provides a composition for remedying an ingrown fingernail or toenail, comprising a siloxane resin including an epoxy siloxane resin, an acrylate-based compound, and a photoinitiator.

In the present disclosure, the composition may comprise 1 to 50% by weight of a siloxane resin, 10 to 50% by weight of an acrylate-based compound, 0.1 to 15% by weight of a photoinitiator, and the remaining amount of solvent, based on the total weight of the composition.

In the present disclosure, the siloxane resin may further comprise a siloxane resin having no epoxy group.

In the present disclosure, the acrylate-based compound may comprise one or more selected from the group consisting of urethane acrylate, epoxy acrylate, silicone-modified acrylate, and polyester acrylate.

In the present disclosure, the acrylate-based compound may be a multifunctional acrylate-based compound having three or more acrylate functional groups.

In the present disclosure, a weight ratio of the siloxane resin and the acrylate-based compound may be 1:1 to 3:1.

In the present disclosure, the photoinitiator may comprise a cationic initiator and a radical initiator.

In the present disclosure, the radical initiator may comprise a short-wavelength radical initiator having a maximum absorption peak at 300 nm or less.

In the present disclosure, a weight ratio of the cationic initiator and the radical initiator may be 1:2 to 1:50.

The composition of the present disclosure may further comprise polythiol.

The composition of the present disclosure may further comprise one or more additives selected from the group consisting of an ultraviolet absorber, a leveling agent, and a polymerization inhibitor.

Advantageous Effects

The composition for remedying an ingrown fingernail or toenail according to the present disclosure may remedy the ingrown fingernail or toenail by generating an inverse curl in a direction opposite to the curved direction of the ingrown fingernail or toenail through a simple method of application and curing. Accordingly, it is possible to provide a continuous effect of remedying in a simple manner without a separate corrective device or surgical operation.

In particular, the present disclosure may provide a composition which is capable of preventing a cured material from being separated from the surface of a fingernail or toenail while maximizing the degree of curl thereof through optimal mixing of the composition, preventing residues from being appearing after curing, and controlling the heat caused by reaction heat so that the temperature thereof does not rise, and thus has effect of remedying an ingrown fingernail or toenail and excellent use convenience.

DESCRIPTION OF DRAWINGS

FIGS. 1 and 2 show the results of a remedy test of a composition for remedying an ingrown fingernail or toenail according to an embodiment of the present disclosure.

BEST MODE

Hereinafter, a specific implementation of the present disclosure will be described in more detail. Unless otherwise defined, all technical and scientific terms used herein have the same meaning as commonly understood by a person skilled in the art to which the present disclosure pertains. In general, the nomenclature used herein is well known and commonly used in the art.

The present disclosure relates to a composition for remedying an ingrown fingernail or toenail, which may be applied to the surface of the ingrown fingernail or toenail and cured to produce an effect of remedying.

According to the present disclosure, when the composition for remedying an ingrown fingernail or toenail is applied to the surface of the fingernail or toenail to be remedied and irradiated with ultraviolet rays, an inverse curl is generated as the composition cured, thereby showing the effect of remedying the ingrown fingernail or toenail. In the present disclosure, the term "inverse curl" refers to a curl generated in a direction opposite to the curved direction of the ingrown fingernail or toenail, and conversely, the term "normal curl" refers to a curl generated in the curved direction of the ingrown fingernail or toenail.

Using the composition according to the present disclosure, it is possible to remedy the ingrown fingernail or toenail without a separate corrective device. Therefore, it does not cause discomfort to the user, and the effect of remedying may be continuously maintained regardless of whether the shoes are worn or not. In addition, in the prior art, when a coating composition was used to remedy the ingrown fingernail or toenail, it simply had the effect of protecting the fingernail or toenail and providing flexibility, but it was difficult to achieve a practical physical effect of remedying. However, using the present disclosure, it is possible to exhibit an effect of remedying by a physical force simply by applying the composition to the fingernail or toenail and irradiating it with ultraviolet rays.

When a commonly used photocurable composition is applied to the surface of the ingrown fingernail or toenail, the shrinkage that occurs during curing can cause a normal curl, which can further worsen the symptoms of the ingrown fingernail or toenail. However, by controlling the components and mixing of a photocurable composition, the present disclosure may provide a composition that may be effectively used for the remedy of the ingrown fingernail or toenail by having both good curability and adhesion while generating an inverse curl.

In order to achieve this effect, a composition for remedying an ingrown fingernail or toenail according to the present disclosure is characterized in that it comprises a siloxane resin, an acrylate-based compound, and a photoinitiator.

The siloxane resin is a photocurable resin and refers to a polysiloxane compound containing a siloxane functional group consisting of Si—O bonds within the molecule. In the present disclosure, the siloxane resin is used as an ingredient to induce an inverse curl during curing.

Specifically, when a composition comprising a siloxane resin according to the present disclosure is applied to the ingrown fingernail or toenail and cured, the composition may be cured while being curved in a direction opposite to the curved direction of the ingrown fingernail or toenail. Therefore, by simply applying and curing the composition, a force may be applied in the opposite direction of the ingrown fingernail or toenail to induce the effect of remedying.

In the present disclosure, the siloxane resin may comprise a polysiloxane resin containing one or more epoxy groups, that is, an epoxy siloxane resin. When an epoxy siloxane resin is used, the degree of curl of an inverse curl may be enhanced and the cured material may have high hardness, which can be excellent for remedying an ingrown fingernail or toenail.

In the present disclosure, the epoxy siloxane resin may comprise an epoxy group at the end of the polysiloxane, and may be represented, for example, by the following Formula 1:

[Formula 1]

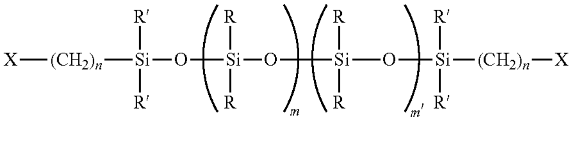

wherein

R may each independently be hydrogen, a $C_1$-$C_6$ alkyl group, or a $C_1$-$C_6$ alkoxy group, R' may each independently be hydrogen, a hydroxy group, a $C_1$-$C_6$ alkyl group, or a $C_1$-$C_6$ alkoxy group, X may each independently be an epoxy group, a $C_1$-$C_6$ epoxyalkoxy group, or a $C_1$-$C_6$ epoxycycloalkyl group, n may be an integer from 1 to 6, and m+m' may be 10 to 1,000.

For example, the epoxy siloxane resin may be prepared by condensation of polysiloxane containing an alkyl group and a silane compound containing an epoxy group.

In an embodiment of the present disclosure, as the siloxane resin the epoxy siloxane resin and a siloxane resin having no epoxy group may be mixed and used. If only epoxy siloxane resin is used as the siloxane resin, there is a possibility that problems with heat generation and uneven curls may occur when irradiated with a UV lamp for nails. In the present disclosure, the above problem may be solved by mixing and using the epoxy siloxane resin with a siloxane resin having no epoxy group.

In the present disclosure, the siloxane resin having no epoxy group may be represented by the following Formula 2:

[Formula 2]

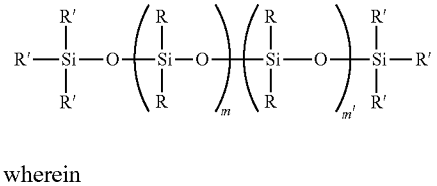

wherein

R may each independently be hydrogen, a $C_1$-$C_6$ alkyl group, or a $C_1$-$C_6$ alkoxy group, R' may each independently be hydrogen, a hydroxy group, a $C_1$-$C_6$ alkyl group, or a $C_1$-$C_6$ alkoxy group, and m+m' may be 10 to 1,000.

In the present disclosure, the siloxane resin having no epoxy group may be a siloxane resin including Si—H bonds in a polysiloxane repeating unit, that is, a hydrosiloxane resin.

The hydrosiloxane resin may be a polysiloxane including an alkylhydrosiloxane repeating unit in the molecule, such as an alkylhydrosiloxane-dialkylsiloxane copolymer, an alkylhydrosiloxane, etc., for example, a compound of Formula 2 wherein one or more R is a hydrogen.

In the present disclosure, the epoxy siloxane resin and the siloxane resin having no epoxy group may be mixed at a ratio of 1:2 to 1:10, preferably 1:3 to 1:8 based on weight. When the content of the siloxane resin is adjusted to the above range, it may be adjusted so that the degree of curl is high, no uncured residue is generated, and no heat appears during curing, as the invers curl occurs evenly on the curved surface of the ingrown fingernail or toenail.

In the present disclosure, the total amount of the siloxane resin may be 1 to 50% by weight, preferably 10 to 50% by weight, and more preferably 20 to 40% by weight, based on the total weight of the composition.

The acrylate-based compound contained in a composition for remedying an ingrown fingernail or toenail according to the present disclosure is a polymerizable compound used together with a siloxane resin. In the present disclosure, the term acrylate is meant to include not only acrylate but also methacrylate, and the term acrylate-based compound is meant to include an acrylate-based polymer, an oligomer, and a monomer.

The acrylate-based compound may be urethane acrylate, epoxy acrylate, silicone-modified acrylate, polyester acrylate, etc., and is preferably a urethane acrylate compound.

The urethane acrylate may be prepared by reacting an acrylate compound having a hydroxy group in the molecule with a compound having an isocyanate group. For example, the urethane acrylate may be a multifunctional urethane acrylate, and may be prepared by reacting a hydroxy acrylate compound containing three or more polymerizable unsaturated functional groups in the molecule with a difunctional aliphatic isocyanate compound.

The bifunctional aliphatic isocyanate compounds may be hexamethylene diisocyanate, dicyclohexylmethane diisocyanate, isophorone diisocyanate, 1,4-diisocyanatobutane, 1,6-diisocyanatohexane, 1,8-diisocyanatooctane, 1,12-diisocyanatododecane, 1,5-diisocyanato-2-methylpentane, trimethyl-1,6-diisocyanatohexane, 1,3-bis(isocyanatomethyl)cyclohexane, trans-1,4-cyclohexene diisocyanate, 4,4'-methylenebis(cyclohexyl isocyanate), toluene-2,4-diisocyanate, toluene-2,6-diisocyanate, xylene-1,4-diisocyanate, tetramethylxylene-1,3-diisocyanate, 1-chloromethyl-2,4-diisocyanate, 4,4'-methylenebis(2,6-dimethylphenylisocyanate), 4,4'-oxybis(phenylisocyanate), etc.

The hydroxy acrylate compounds containing three or more polymerizable unsaturated functional groups in the molecule may be pentaerythritol triacrylate, dipentaerythritol triacrylate, pentaerythritol tri/tetra(meth)acrylate, dipentaerythritol penta/hexa(meth)acrylate, etc.

In the present disclosure, the acrylate-based compound may be a multifunctional acrylate compound having three or more acrylate groups. Here, the number of functional groups is preferably 5 to 20, and more preferably 8 to 18.

In the present disclosure, when the number of functional groups in the acrylate-based compound is small, a normal curl, not an inverse curl, is induced, and thus the total degree of curl may be reduced, and a rate at which the degree of curl changes may be reduced. Accordingly, the effect of remedying on the ingrown fingernail or toenail may be insignificant, or rather, the ingrown fingernail or toenail may be worsened by the normal curl. However, as the number of functional groups in the acrylate-based compound increases to 3 or more, preferably 5 or more, and more preferably 8 or more, the rate of curl generation and the degree of curl may be increased, thereby exhibiting an excellent effect on remedying the ingrown fingernail or toenail.

In the present disclosure, the content of the acrylate-based compound may be 10 to 50% by weight, and preferably 15 to 35% by weight, based on the total weight of the composition.

In the present disclosure, a weight ratio of the siloxane resin and the acrylate-based compound may be 1:1 to 3:1, and is preferably 1:1 to 2:1. In the above range, as the composition according to the present disclosure cured, an inverse curl is generated and the degree of curl is increased, thereby improving the effect of remedying the introverted fingernail or toenail, and even when cured with a UV lamp for nails, no residue remains after curing and excellent hardness may be exhibited.

The photoinitiator contained in a composition for remedying an ingrown fingernail or toenail according to the present disclosure is a component that polymerizes a resin and a polymerizable compound by irradiation with light. The photoinitiator may be contained in an amount of 0.1 to 15% by weight, and preferably 2 to 10% by weight, based on the total weight of the composition.

In the present disclosure, as the photoinitiator, a cationic initiator or a radical initiator may be used, and preferably a cationic initiator and a radical initiator may be mixed and used.

In the present disclosure, the cationic initiator is an initiator that initiates polymerization by forming cations by irradiation with light, and in the present disclosure, the cationic initiator is used as a component to induce an inverse curl.

In the present disclosure, as the cationic initiator, onium salt may be used. Specifically, the onium salt initiator may refer to an iodonium salt, a sulfonium salt, etc., and may include, for example, one or more selected from the group consisting of sulfonium hexafluorophosphate, diphenyl(4-phenylthio)phenylsulfonium hexafluorophosphate, (phenyl)[4-(2-methylpropyl)phenyl]-iodonium hexafluorophosphate, (thiodi-4,1-phenylene)bis(diphenylsulfonium) dihexafluoroantimonate, and (thiodi-4,1-phenylene)bis(diphenylsulfonium) dihexafluorophosphate.

In addition to the above, as a cationic initiator, it is also possible to use organometallic salts such as iron-arene complexes; organic silanes such as o-nitrilebenzyl triaryl silyl ether, triaryl silyl peroxide, and acyl silane; latent sulfuric acids such as alpha-sulfonyloxyketone and alpha-hydroxymethylbenzoin sulfonate.

The content of the cationic initiator may be 0.05 to 5% by weight, and preferably 0.1 to 3% by weight, based on the total weight of the composition. In the above range, the cationic initiator can minimize the yellowing phenomenon during curing, while the inverse curl phenomenon can occur.

In the present disclosure, the radical initiator is an initiator that initiates polymerization by forming radicals by irradiation with light. In the present disclosure, the radical initiator is used to induce curing of the composition while controlling shrinkage from occurring.

The radical initiator may be classified into a short-wavelength initiator and a long-wavelength initiator depending on an absorption wavelength region. In the present disclosure, the radical initiators are preferably a short-wavelength initiator. In the present disclosure, the term “short-wavelength initiator” may refer to an initiator that exhibits a maximum absorption peak at a wavelength of 300 nm or less, and preferably 250 nm or less.

If the long-wavelength initiator is used as the radical initiator, the composition may be shrunk while being curved in the curved direction of the fingernail or toenail when cured. As a result, problems may appear that reduce the effect of remedying the ingrown fingernail or toenail and actually worsen the disease. In the present disclosure, by using the short-wavelength initiator as the radical initiator, it is possible to adjust the inverse curl to appear without shrinkage during curing.

The radical initiator used in the present disclosure may be, for example, 1-hydroxycyclohexylphenylketone, 2-hydroxy-2-methyl-1-phenylpropane-1-phenone, 2-hydroxy-2-methyl-1-phenyl-1-propanone, cyclohexylphenylketone, benzophenone, 1-(4-isopropylphenyl)-2-hydroxy-2-methyl-1-one, 1-[4-(2-hydroxyethoxy)phenyl]-2-hydroxy-2-methylpropan-1-one, α,α-diethoxyacetophenone, etc.

The content of the radical initiator may be 0.05 to 10% by weight, and preferably 2 to 8% by weight, based on the total weight of the composition. In addition, when the cationic initiator and the radical initiator are mixed and used, the weight ratio may be 1:2 to 1:50, and preferably 1:10 to 1:30. Within the above range, it is possible to induce an inverse curl to achieve an excellent effect of remedying an ingrown fingernail or toenail, while minimizing a yellowing phenomenon and to adjust so that no uncured residue remains on the surface.

In an embodiment of the present disclosure, the composition for remedying an ingrown fingernail or toenail may further comprise polythiol.

In the present disclosure, the polythiol is an ingredient that improves the effect of remedying an ingrown fingernail or toenail by promoting surface curing and maintaining an inverse curl by the ingredients of the present disclosure.

The polythiol may comprise one or more selected from the group consisting of pentaerythritol tetrakis(3-mercaptopropionate), 4-mercaptomethyl-1,8-dimercapto-3,6-dithioctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 1,1,3,3-tetrakis(mercaptomethylthio)propane, 4,6-bis(mercaptomethylthio)-1,3-dithian, 2-(2,2-bis(mercaptomethylthio)ethyl)-1,3-dithiaethane, 1,1,2,2-tetrakis(mercaptomethylthio)ethane, and 3-mercaptomethyl-1,5-dimercapto-2,4-dithiapentane.

In the present disclosure, the content of the polythiol may be 2 to 10% by weight, and preferably 5 to 8% by weight, based on the total weight of the composition. Within the above range, the cured material may exhibit excellent hardness while maintaining the effect of inducing an inverse curl.

The composition for remedying an ingrown fingernail or toenail according to the present disclosure may further comprise an ultraviolet (UV) absorber.

In the present disclosure, the ultraviolet absorber is contained in an amount of 0.05 to 3% by weight, based on the total weight of the composition, and may have the effect of preventing the cured material being separated from the surface of the fingernail or toenail by adjusting the speed at which an inverse curl occurs during curing.

The ultraviolet absorber may be one or more selected from the group consisting of benzoxazinone-based, triazine-based, benzotriazole-based, and benzophenone-based ultraviolet absorbers. Examples of commercially available ultraviolet absorbers include benzoxazinone-based UV absorbers such as CYASORB UV-3853S from Cytec; triazine-based UV absorbers such as CYASORB UV-1164 from Cytec, TINUVIN 1577, TINUVIN P, TINUVIN 234, TINUVIN 326, TINUVIN 328, TINUVIN 329, TINUVIN 571, TINUVIN 400, and TINUVIN 479 from BASF; benzotriazole-based UV absorbers such as CYASORB UV-2337 and CYASORB UV-5411 from Ciba, TINUVIN 360, TINUVIN 213, TINUVIN 99-2, TINUVIN 171, TINUVIN 328, TINUVIN 384-2, TINUVIN 900, TINUVIN 928, and TINUVIN 1130 from BASF, SONGSORB 1000, SONGSORB 2340, SONGSORB 3200, SONGSORB 3260, SONGSORB 3270, and SONGSORB 3280 from Songwon Industrial Co., Ltd.; benzophenone-based UV absorbers such as CYASORB UV-9, CYASORB UV-24, and CYASORB UV-531 from Cytec, CHIMASSORB 81 from Ciba, SONGSORB 8100 from Songwon Industrial Co., Ltd., etc., and each UV absorber may be used alone or in a mixture of two or more.

The composition for remedying an ingrown fingernail or toenail according to the present disclosure may further comprise a leveling agent to prevent a cratering phenomenon of the surface. The leveling agent may be contained in an amount of 0.1 to 1% by weight, based on the total weight of the composition in consideration of coating properties and curability.

In the present disclosure, the leveling agent may be a silicone-based agent, a fluorine-based agent, or an acrylic-based agent, etc. Examples of commercially available leveling agents include BYK-323, BYK-331, BYK-333, BYK-337, BYK-373, BYK-375, BYK-377, and BYK-378 from BYK-Chemie GmbH; TEGO Glide 410, TEGO Glide 411, TEGO Glide 415, TEGO Glide 420, TEGO Glide 432, TEGO Glide 435, TEGO Glide 440, TEGO Glide 450, TEGO Glide 455, TEGO Rad 2100, TEGO Rad 2200N, TEGO Rad 2250, TEGO Rad 2300, and TEGO Rad 2500 from Daegu Corporation; FC-4430 and FC-4432 from 3M Company.

The composition for remedying an ingrown fingernail or toenail according to the present disclosure may further contain 0.1 to 1% by weight of a polymerization inhibitor, based on the total weight of the composition.

In the present disclosure, examples of the polymerization inhibitor include phenolic compounds such as hydroquinone, hydroquinone monomethyl ether, hydroquinone monoethyl ether, p-methoxyphenol, and p-t-butylcatechol, hydroxylamine compounds such as N,N-diethylhydroxylamine and N-nitrosophenylhydroxylamine ammonium salt (cuperone), organosulfur compounds such as dithiobenzoyl disulfide and tetraethylthiuram disulfide, etc., and each polymerization inhibitor may be used alone or in a mixture of two or more.

The composition for remedying an ingrown fingernail or toenail according to the present disclosure may be mixed with a solvent and used.

The solvent may be an organic solvent commonly used as a solvent for coating compositions. For example, the organic solvent may include one or more solvents such as methanol, ethanol, isopropanol, butanol, methyl cellosolve, ethyl cellosolve, methyl ethyl ketone, methyl butyl ketone, methyl isobutyl ketone, diethyl ketone, dipropyl ketone, cyclohexanone, hexane, heptane, octane, benzene, toluene, xylene, methyl acetate, ethyl acetate, propyl acetate, isopropyl acetate, butyl acetate, and methoxymethyl ethyl acetate.

In addition to the above components, the composition for remedying an ingrown fingernail or toenail according to the present disclosure may further contain components commonly added to photocurable compositions, for example, ultraviolet stabilizers, antioxidants, wetting agents, anti-foaming agents, etc.

According to the present disclosure, the composition for remedying an ingrown fingernail or toenail may be applied on the ingrown fingernail or toenail to be remedied and dried with a UV lamp to form a coating layer. Here, the coating layer may be formed one or more times, and preferably 2 to 4 times to adjust the effect of remedying, and to control a natural occurrence of the inverse curl without separation of the coating layer. In addition, after applying a top coat on the uppermost coating layer, curing may be completed by finally irradiating with ultraviolet rays.

The application thickness of the composition may be 1 to 500 μm per time, and preferably 10 to 200 μm. UV drying may be performed for 10 seconds or more per time, and preferably 10 seconds to 1 minute.

The specifications of the UV lamp used for drying (curing) the composition are not particularly limited. For example, as a UV lamp commonly used in nail shops, a lamp that emit a wavelength within the range of 300 to 450 nm and has a power of 50 to 100 W may be used.

When the composition for remedying an ingrown fingernail or toenail according to the present disclosure is applied to the fingernail or toenail and irradiated with light, the composition is curved in the direction opposite to the curved direction of the fingernail or toenail while being cured. As a result, the effect of a physical force being applied to both ends of the ingrown fingernail or toenail in the direction opposite to the curved direction appears, making it possible to remedy the ingrown fingernail or toenail.

According to the present disclosure, an ingrown fingernail or toenail may be easily remedied simply by applying and curing a coating agent, without surgery or corrective devices. In addition, by using the present disclosure, the effect of remedying may be continuously maintained without causing inconvenience to life. Moreover, in the present disclosure, the effect of remedying was improved by maximizing the degree of curl while generating an inverse curl through the optimal mixing of the composition, preventing problems of shrinkage or separation from the adhered surface during curing, and adjusting the composition to be easily cured. Accordingly, the present disclosure can provide a technology of remedying an ingrown fingernail or toenail that exhibits excellent effect of remedying by means of a simple and convenient method.

EXAMPLES

Hereinafter, the present disclosure will be described in more detail with reference to Examples. However, these Examples show some experimental methods and configurations to illustratively illustrate the present disclosure, and the scope of the present disclosure is not limited to these Examples.

Preparation Example: Preparation of Composition for Remedying Ingrown Fingernail or Toenail A composition for remedying an ingrown fingernail or toenail was prepared according to the composition shown in Table 1 below (unit: wt %).

TABLE 1

| Components | | Preparation Example 1 | Preparation Example 2 | Preparation Example 3 | Preparation Example 4 | Preparation Example 5 | Preparation Example 6 | Preparation Example 7 |
|---|---|---|---|---|---|---|---|---|
| Siloxane resin | Epoxy siloxane | 5 | 5 | 5 | 5 | 5 | 5 | — |
| | Siloxane having no epoxy group | 25 | 25 | 25 | 25 | 25 | 25 | 25 |
| Urethane acrylate | Pentadeca functional | 23 | 23 | — | 23 | 23 | 28.8 | 28 |
| | Hexa functional | — | — | 23 | — | — | — | — |
| Polythiol | | 6.4 | 6.4 | 6.6 | 6.6 | 6.8 | — | 6.4 |
| Cationic initiator | | 0.2 | 0.2 | 0.2 | 0.2 | — | 1 | 0.2 |
| Radical initiator | Short-wavelength initiator | 5 | 5 | 5 | — | 5 | 5 | 5 |
| | Long-wavelength initiator | — | — | — | 5 | — | — | — |
| UV absorber | | 0.1 | — | — | — | — | — | 0.1 |
| Leveling agent | | 0.2 | 0.2 | 0.2 | 0.2 | 0.2 | 0.2 | 0.2 |
| Polymerization inhibitor | | 0.1 | 0.2 | — | — | — | — | 0.1 |
| Solvent | PGMA | 15 | 15 | 15 | 15 | 15 | 15 | 15 |
| | MIBK | 20 | 20 | 20 | 20 | 20 | 20 | 20 |

A description of the ingredients used in Table 1 above is as follows.

Epoxy siloxane: Epoxypropoxypropyl dimethoxysilyl polydimethylsiloxane (Company C)

Siloxane having no epoxy group: Methylhydrosiloxane (Company G)

Pentadecafunctional urethane acrylate: POLYGOMER PN-3915 (Company P)

Hexafunctional urethane acrylate: POLYGOMER PN-3640 (Company P)

Polythiol: tetrafunctional polythiol (Company S)

Cationic initiator: Sulfonium hexafluorophosphate (Omnicat 270, Company I)

Short-wavelength radical initiator: 1-hydroxycyclohexylphenylketone (Omnirad 184, Company I)

Long-wavelength radical initiator: 2,4,6-trimethylbenzoyl-diphenyl phosphine oxide (Omnirad TPO, Company I)

UV absorber: Hydroxylphenyl triazine (Tinuvin 400, Company B)

Leveling agent: Silicone-free acryl-based leveling agent (TEGO Flow 460 N, Company E)

Polymerization inhibitor: Hydroquinone monomethyl ether (MEHQ)

PGMA: 2-methoxy-1-methylethyl acetate

MIBK: Methyl isobutyl ketone

Comparative Example: Preparation of Photocurable Composition Containing Siloxane Resin In order to compare the properties of the photocurable composition applied to conventional display coatings with the composition according to the present disclosure, a photocurable composition for displays containing an epoxy siloxane resin was prepared as a comparative example.

Specifically, a photocurable composition containing 10.3% by weight of epoxy siloxane resin, 58.6% by weight of urethane acrylate (dipentaerythritol hexaacrylate), 1.4% by weight of (4-methylphenyl)[4-(2-methylpropyl)phenyl] iodonium hexafluorophosphate (cationic initiator). 2.1% by weight of 1-hydroxycyclohexylphenylketone (radical initiator), 3.4% by weight of methyl-5-norbornene-2,3-dicarboxylic anhydride (curing agent), and 24.1% by weight of methyl ethyl ketone (solvent) was prepared.

Experimental Example 1: Measurement of Degree of Curl and Confirmation of Degree of Curing After Curing The composition for remedying an ingrown fingernail or toenail prepared in the above Preparation Example was applied to a 0.5 T thick artificial nail tip with a thickness of 20 μm, dried with a UV LED nail lamp for 30 seconds, and then application and drying were repeated under the same conditions. As the UV LED nail lamp, a lamp with a power of 70 W in the 365-405 nm wavelength range was used, according to the specifications of the lamp commonly used in nail shops.

The degree of opening of the nail tip in the first application and drying results and the second application and drying results, as well as the degree of opening of the nail tip after being stored indoors for 24 hours, were measured and shown in Table 2 below (unit: mm). Here, the degree of an inverse curl was expressed as a positive number, and the degree of a normal curl was expressed as a negative number.

In addition, after curing, the residue was checked on the surface. If there was no uncured residue on the surface or the amount thereof was small, it was indicated as ○, and if a large amount of residue was observed, it was indicated as X. The results are shown in Table 2.

TABLE 2

| Category | After one application | After two applications | After 24 hours of storage | Degree of curing of surface |
|---|---|---|---|---|
| Preparation Example 1 | 0.3 | 0.7 | 1.2 | ○ |
| Preparation Example 2 | 0.2 | 0.6 | 1.0 | ○ |
| Preparation Example 3 | 0 | 0.3 | 0.6 | ○ |
| Preparation Example 4 | 0 | −0.3 | −0.5 | ○ |
| Preparation Example 5 | 0 | 0 | −0.2 | X |
| Preparation Example 6 | 0.2 | 0.6 | 1.0 | ○ |
| Preparation Example 7 | 0 | 0 | 0.2 | X |

According to the results in Table 2, it was confirmed that when the composition of Preparation Example 1 was applied to the nail tip, the inverse curl occurred, and after 24 hours, the degree of curl was as high as 1.2 mm, and curing was completed without any residue.

Meanwhile, in Preparation Example 2, the inverse curl occurred, and 24 hours, the degree of curl was 1.0 mm, and curing was completed without any residue. However, in Preparation Example 2, since the UV absorber was not included, the degree of curl was slightly reduced compared to Preparation Example 1, and heat was generated when applied to the toenail surface.

In Preparation Example 3, an acrylate-based compound having the same level of viscosity as the compound used in Preparation Example 1 and having a small number of functional groups was used. As a result of the experiment, it was confirmed that after 24 hours, the degree of curl was reduced to 0.6 mm, which was half of Preparation Example 1. Accordingly, it could be confirmed that the higher the number of functional groups in the acrylate-based compound, the greater of opening of the nail tip and the degree of curl.

The compositions of Preparation Example 4 using a long-wavelength initiator as a radical initiator, and Preparation Example 5 using only a radical initiator as a photoinitiator, without a cationic initiator, shrunk upon curing, resulting in a normal curl rather than an inverse curl, and accordingly, the ingrown fingernail or toenails were rather deteriorated. In addition, in Preparation Example 5 without a cationic initiator, uncured residue was observed on the surface.

Furthermore, in Preparation Example 6, where polythiol was excluded from the mixing, it was confirmed that the inverse curl occurred and the degree of curl was similar to that of Preparation Example 2. However, despite increasing the content of acrylate-based compounds and cationic initiators to achieve a high curing reaction, some uncured residues were observed on the surface, and it was confirmed that it is desirable to use polythiol to increase the degree of curl of the inverse curl and secure curability to maintain the effect of remedying.

In Preparation Example 7 which does not include an epoxy siloxane resin, shrinkage occurred due to curing, resulting in a very low degree of curl, and despite an increase in the amount of the acrylate-based compound, hardness was significantly lowered.

According to the above experimental results, it was confirmed that when using an epoxy siloxane resin as a siloxane resin, using a compound with a high number of functional groups as an acrylate-based compound, and using a mixture of a cationic initiator and a short-wavelength radical initiator as a photoinitiator, an inverse curl occurs during curing and force was applied in the opposite direction of the curvature of the nail tip, providing the remedy effect. Also, it was confirmed that when polythiol was mixed, the degree of curl was increased and curability was improved, thereby further improving the effect of remedying.

Experimental Example 2: Remedy Test for Ingrown Toenail

For two test subjects, a composition for remedying ingrown fingernail or toenail of Preparation Example 1 was applied to the fingernail or toenail in the same manner as in Experimental Example 1 and cured, and then the effect of remedying was observed.

FIGS. 1 and 2 are photographs of the results of the above experiment, and when the composition according to the present disclosure was applied to both test subjects, the curvature of both ends of the toenail became gentler.

Accordingly, it could be confirmed that the composition for remedying ingrown fingernail or toenail according to the present disclosure actually exhibited the effect of remedying the ingrown toenail.

Experimental Example 3: Comparison of Curing Properties With Photocurable Compositions for Displays The photocurable composition of Comparative Example was cured under the same conditions as Experimental Example 1, and then the curl properties were observed.

As a result, it was confirmed that an inverse curl did not occur evenly on the curved surface of the nail tip and that cracks appeared in the cured material. Accordingly, it was confirmed that the photocurable composition for displays that requires a high crosslinking density and thus contains a high mixing amount of polymerizable compounds, had low flexibility, making it difficult to apply it to curved surface such as an ingrown fingernail or toenail.

In addition, as a result of irradiating ultraviolet rays with a UV nail lamp rather than the UV lamp used in the display industry, high reaction heat was generated, and there was a risk of burns when applied to an ingrown fingernail or toenail.

On the other hand, in Experimental Example 1 it was confirmed that the composition for remedying an ingrown fingernail or toenail satisfying the composition according to the present disclosure, had a high degree of curl while an inverse curl occurred, had excellent flexibility and thus, may maintain an inverse curl even on the curved surface, and had excellent surface hardness. Thus, it could be confirmed that the composition according to the present disclosure exhibits characteristics optimized for remedying an ingrown fingernail or toenail, unlike conventional photocurable compositions used in the electronic device industry such as displays.

Although some embodiments of the present disclosure have been described above, the present disclosure is not limited to the above-described embodiments, but may be implemented with modifications and variations without departing from the gist of the present disclosure, and it is to be understood that the forms in which such modifications and variations are made also fall within the technical idea of the present disclosure.

The invention claimed is:

1. A composition for remedying an ingrown fingernail or toenail, comprising a siloxane resin comprising an epoxy siloxane resin, an acrylate-based compound, and a photoinitiator.

2. The composition for remedying an ingrown fingernail or toenail of claim 1, wherein the composition comprises 1 to 50% by weight of the siloxane resin, 10 to 50% by weight of the acrylate-based compound, 0.1 to 15% by weight of the photoinitiator, and the remaining amount of solvent, based on the total weight of the composition.

3. The composition for remedying an ingrown fingernail or toenail of claim 1, wherein the siloxane resin further comprises a siloxane resin having no epoxy group.

4. The composition for remedying an ingrown fingernail or toenail of claim 1, wherein the acrylate-based compound comprises one or more selected from the group consisting of urethane acrylate, epoxy acrylate, silicone-modified acrylate, and polyester acrylate.

5. The composition for remedying an ingrown fingernail or toenail of claim 1, wherein the acrylate-based compound is a multifunctional acrylate-based compound having three or more acrylate functional groups.

6. The composition for remedying an ingrown fingernail or toenail of claim 1, wherein a weight ratio of the siloxane resin and the acrylate-based compound is 1:1 to 3:1.

7. The composition for remedying an ingrown fingernail or toenail of claim 1, wherein the photoinitiator comprises a cationic initiator and a radical initiator.

8. The composition for remedying an ingrown fingernail or toenail of claim 7, wherein the radical initiator comprises a short-wavelength radical initiator having a maximum absorption peak at 300 nm or less.

9. The composition for remedying an ingrown fingernail or toenail of claim 7, wherein a weight ratio of the cationic initiator and the radical initiator is 1:2 to 1:50.

10. The composition for remedying an ingrown fingernail or toenail of claim 1, further comprising polythiol.

11. A method for remedying an ingrown fingernail or toenail, comprising: applying onto a fingernail or toenail of a subject in need thereof a composition comprising a siloxane resin comprising an epoxy siloxane resin, an acrylate-based compound, and a photoinitiator; and curing the composition.

12. The method for remedying an ingrown fingernail or toenail of claim 11, wherein the composition comprises 1 to 50% by weight of the siloxane resin, 10 to 50% by weight of the acrylate-based compound, 0.1 to 15% by weight of the photoinitiator, and the remaining amount of solvent, based on the total weight of the composition.

13. The method for remedying an ingrown fingernail or toenail of claim 11, wherein the siloxane resin further comprises a siloxane resin having no epoxy group.

14. The method for remedying an ingrown fingernail or toenail of claim 11, wherein the acrylate-based compound comprises one or more selected from the group consisting of urethane acrylate, epoxy acrylate, silicone-modified acrylate, and polyester acrylate.

15. The method for remedying an ingrown fingernail or toenail of claim 11, wherein the acrylate-based compound is a multifunctional acrylate-based compound having three or more acrylate functional groups.

16. The method for remedying an ingrown fingernail or toenail of claim 11, wherein a weight ratio of the siloxane resin and the acrylate-based compound is 1:1 to 3:1.

17. The method for remedying an ingrown fingernail or toenail of claim 11, wherein the photoinitiator comprises a cationic initiator and a radical initiator.

18. The method for remedying an ingrown fingernail or toenail of claim 17, wherein the radical initiator comprises a short-wavelength radical initiator having a maximum absorption peak at 300 nm or less.

19. The method for remedying an ingrown fingernail or toenail of claim 17, wherein a weight ratio of the cationic initiator and the radical initiator is 1:2 to 1:50.

20. The method for remedying an ingrown fingernail or toenail of claim 11, wherein the composition further comprises polythiol.

* * * * *